(12) United States Patent
Sterimbaum et al.

(10) Patent No.: US 7,812,168 B2
(45) Date of Patent: Oct. 12, 2010

(54) PURIFICATION OF MONTELUKAST

(75) Inventors: Greta Sterimbaum, Rishon-Lezion (IL); Evgeny Shapiro, Haifa (IL); Kobi Chen, Kfar-Saba (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 995 days.

(21) Appl. No.: 11/481,877

(22) Filed: Jul. 5, 2006

(65) Prior Publication Data

US 2007/0078158 A1 Apr. 5, 2007

Related U.S. Application Data

(60) Provisional application No. 60/697,000, filed on Jul. 5, 2005.

(51) Int. Cl.
C07D 215/38 (2006.01)
(52) U.S. Cl. ........................ 546/159; 546/153
(58) Field of Classification Search ............... 546/153, 546/159
See application file for complete search history.

(56) References Cited

U.S. PATENT DOCUMENTS

| | | | |
|---|---|---|---|
| 4,851,409 A | 7/1989 | Young et al. | |
| 5,266,568 A | 11/1993 | Belley et al. | |
| 5,428,033 A | 6/1995 | Belley et al. | |
| 5,506,227 A | 4/1996 | Zamboni et al. | |
| 5,523,477 A | 6/1996 | King et al. | |
| 5,565,473 A | 10/1996 | Belley et al. | |
| 5,614,632 A | 3/1997 | Bhupathy et al. | |
| 5,856,322 A | 1/1999 | Belley et al. | |
| 5,869,673 A | 2/1999 | Tung et al. | |
| 5,952,347 A | 9/1999 | Arison et al. | |
| 6,320,052 B1 | 11/2001 | Bhupathy et al. | |
| 6,333,198 B1 | 12/2001 | Edmeades et al. | |
| 7,189,853 B2 * | 3/2007 | Sundaram et al. | 546/180 |
| 7,271,268 B1 | 9/2007 | Suen et al. | |
| 7,417,149 B2 * | 8/2008 | Turchetta et al. | 546/174 |
| 7,547,787 B2 * | 6/2009 | Shapiro et al. | 546/157 |
| 2005/0107426 A1 | 5/2005 | Overeem et al. | |
| 2005/0107612 A1 | 5/2005 | Reguri et al. | |
| 2005/0187243 A1 | 8/2005 | Niddam-Hildesheim et al. | |
| 2005/0234241 A1 | 10/2005 | Sundaram et al. | |
| 2005/0256156 A1 | 11/2005 | Shapiro et al. | |
| 2006/0004204 A1 | 1/2006 | Reguri et al. | |
| 2006/0223999 A1 | 10/2006 | Shen et al. | |
| 2008/0097104 A1 | 4/2008 | Hung et al. | |
| 2008/0146809 A1 | 6/2008 | Satyanarayana et al. | |
| 2008/0188664 A1 | 8/2008 | Brand et al. | |

FOREIGN PATENT DOCUMENTS

| | | |
|---|---|---|
| CN | 1420113 | 5/2003 |
| CN | 1428335 | 7/2003 |
| CN | 1171873 | 4/2004 |
| EP | 0 480 717 | 4/1992 |
| EP | 0 500 360 | 8/1992 |
| EP | 737186 | 10/1996 |
| WO | WO 95/18107 | 7/1995 |
| WO | WO 99/065888 | 12/1999 |
| WO | WO 03/066598 | 8/2003 |
| WO | WO 2004/091618 | 10/2004 |
| WO | WO 2004/108679 | 12/2004 |
| WO | WO 2005/040123 | 5/2005 |
| WO | WO 2005/073194 | 8/2005 |
| WO | WO 2005/074893 | 8/2005 |
| WO | WO 2005/075427 | 8/2005 |
| WO | WO 2005/105749 | 11/2005 |
| WO | WO 2005/105750 | 11/2005 |
| WO | WO 2005/117837 | 12/2005 |
| WO | WO 2006/008751 | 1/2006 |
| WO | WO 2006/021974 | 3/2006 |
| WO | WO 2006/043846 | 4/2006 |
| WO | WO 2006/054317 | 5/2006 |
| WO | WO 2006/058545 | 6/2006 |
| WO | WO 2006/064269 | 6/2006 |
| WO | WO 2007/004237 | 1/2007 |
| WO | WO 2007/012075 | 1/2007 |
| WO | WO 2007/051828 | 5/2007 |
| WO | WO 2007/057225 | 5/2007 |
| WO | WO 2007/059325 | 5/2007 |
| WO | WO 2007/069261 | 6/2007 |
| WO | WO 2007/072114 | 6/2007 |
| WO | WO 2007/096875 | 8/2007 |
| WO | WO 2007/096889 | 8/2007 |
| WO | WO 2007/101841 | 9/2007 |
| WO | WO 2007/107297 | 9/2007 |
| WO | WO 2007/116240 | 10/2007 |
| WO | WO 2008/009970 | 1/2008 |
| WO | WO 2008/015703 | 2/2008 |
| WO | WO 2008/017667 | 2/2008 |
| WO | WO 2008/017669 | 2/2008 |
| WO | WO 2008/023044 | 2/2008 |
| WO | WO 2008/032099 | 3/2008 |
| WO | WO 2008/035086 | 3/2008 |
| WO | WO 2008/035379 | 3/2008 |
| WO | WO 2008/049922 | 5/2008 |

(Continued)

OTHER PUBLICATIONS

King, et al., "An Efficient Synthesis of LTD$_4$ Antagonist L-699,392", *J. Org. Chem.*, 1993, pp. 3731-3735, vol. 58, No. 14.

(Continued)

*Primary Examiner*—D. Margaret Seaman
(74) *Attorney, Agent, or Firm*—Kenyon & Kenyon LLP (57) ABSTRACT

The present invention provides methods of purifying montelukast, a new isolated impurity of montelukast, method for its isolation, and method of using montelukast impurity as a reference marker and a reference standard.

5 Claims, 5 Drawing Sheets

FOREIGN PATENT DOCUMENTS

| WO | WO 2008/058118 | 5/2008 |
| --- | --- | --- |
| WO | WO 2008/062478 | 5/2008 |
| WO | WO 2008/072872 | 6/2008 |
| WO | WO 2008/083635 | 7/2008 |
| WO | WO 2008/098965 | 8/2008 |
| WO | WO 2008/126075 | 10/2008 |
| WO | WO 2008/136693 | 11/2008 |

OTHER PUBLICATIONS

Labelle, et al., "Discovery of MK-0476, A Potent and Orally Active Leukotriene $D_4$ Receptor Antagonist Devoid of Peroxisomal Enzyme Induction", *Bioorg. Med. Lett.*, 1995, pp. 283-288, vol. 5, No. 3.

Snyder, et al., *Introduction to Modern Liquid Chromatography, Second Ed.*, 1979, pp. 549, 552, 571-572.

Strobel, et al., *Chemical Instrumentation: A Systematic Approach, Third Ed.*, 1989, pp. 391-393, 894, 922, 924-925, 953.

Third Party Observation filed for European Application No. 067863696.2101, dated Jan. 30, 2009.

Third Party Observation filed for European Application No. 067863696.2101, dated Mar. 16, 2009.

Saravanan, et al. "Identification, synthesis, isolation and spectral characterization of potential impurities of montelukast sodium", Journal of Pharmaceutical and Biomedical Analysis, 48(3), 708-718 (2008).

Satyanarayana, et al., "New and Improved Synthesis of Montelukast, an Anti-Asthmatic Drug", Synthetic Communications, 37(4): 545-549 (2007).

Dufresne et al.,"Synthesis of Montelukast (MK-0476) Metabolic Oxidation Products", Journal of Organic Chemistry, (61) 8518-8525 (1996).

Third Party Observation filed for European Application No. 067863696.2101, Jan. 26, 2009.

Office Action from related U.S. Appl. No. 11/048,283, mailed Feb. 7, 2008.

Office Action from related U.S. Appl. No. 11/048,276, mailed Feb. 20, 2008.

Office Action from related U.S. Appl. No. 11/601,113, mailed Oct. 22, 2007, and office action mailed Aug. 14, 2008.

\* cited by examiner

PURIFICATION OF MONTELUKAST

CROSS-REFERENCE TO RELATED APPLICATIONS

The present application claims the benefit of the following U.S. Provisional Patent Application No. 60/697,000 filed Jul. 5, 2005. The contents of which are incorporated herein by reference.

FIELD OF INVENTION

The present invention relates to methods for obtaining pure montelukast sodium and to a new isolated impurity of montelukast.

BACKGROUND OF THE INVENTION

Montelukast is a selective, orally active leukotriene receptor antagonist that inhibits the cysteinyl leukotriene $CysLT_1$ receptor. Leukotrienes are associated with the inflammation and constriction of airway muscles and the accumulation of fluid in the lungs. Montelukast sodium is a useful therapeutic agent for treating respiratory diseases such as asthma and allergic rhinitis.

The chemical name for montelukast sodium is: [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetic acid, monosodium salt. Montelukast sodium is a hygroscopic, optically active, white to off-white powder. Montelukast sodium is freely soluble in methanol, ethanol, and water and practically insoluble in acetonitrile.

Montelukast sodium salt is represented by the structure:

U.S. Pat. No. 5,565,473 discloses a synthetic process for preparing montelukast sodium, wherein the compound is obtained as an oil that is then dissolved in water and freeze-dried.

The amorphous form of montelukast sodium is disclosed in U.S. Pat. No. 6,320,052 and WO 03/066598. The '052 patent discloses that the amorphous form is "not ideal for pharmaceutical formulation." Col. 1, lines 64-67. The '052 patent also discloses that the available processes for crystallizing montelukast sodium are "not particularly suitable for large-scale production" because of the "tedious chromatographic purification" technique required and because the "product yields are low." Col. 1, lines 61-64. The '052 patent discloses that in available processes, the free acids are "converted directly to the corresponding sodium salts." Col. 1, lines 58-61. The '052 patent also discloses a crystalline form of montelukast sodium prepared from a solution of toluene and water and then acetonitrile (ACN) with seeding. See Example 8. Seeding is the use of a small amount of crystalline montelukast to induce crystallization in a larger sample.

U.S. Pat. Nos. 5,614,632 and 6,320,052 disclose a process of preparing montelukast sodium salt via the dicyclohexylamine salt.

Like any synthetic compound, montelukast can contain extraneous compounds or impurities that can come from many sources. They can be unreacted starting materials, by-products of the reaction, products of side reactions, or degradation products. Impurities in montelukast or any active pharmaceutical ingredient (API) are undesirable and, in extreme cases, might even be harmful to a patient being treated with a dosage form containing the API.

It is also known in the art that impurities in an API may arise from degradation of the API itself, which is related to the stability of the pure API during storage, and the manufacturing process, including the chemical synthesis. Process impurities include unreacted starting materials, chemical derivatives of impurities contained in starting materials, synthetic by-products, and degradation products.

In addition to stability, which is a factor in the shelf life of the API, the purity of the API produced in the commercial manufacturing process is clearly a necessary condition for commercialization. Impurities introduced during commercial manufacturing processes must be limited to very small amounts, and are preferably substantially absent. For example, the ICH Q7A guidance for API manufacturers requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process.

The product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during processing of an API, such as (R)-montelukast, it must be analyzed for purity, typically, by HPLC or TLC analysis, to determine if it is suitable for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and, thus, are as safe as possible for clinical use. As discussed above, in the United States, the Food and Drug Administration guidelines recommend that the amounts of some impurities be limited to less than 0.1 percent.

Generally, side products, by-products, such as MLK-D, and adjunct reagents (collectively "impurities") are identified spectroscopically and/or with another physical method, and then associated with a peak position, such as that in a chromatogram, or a spot on a TLC plate. (Strobel p. 953, Strobel, H. A.; Heineman, W. R., Chemical Instrumentation: A Systematic Approach, 3rd dd. (Wiley & Sons: New York 1989)). Thereafter, the impurity can be identified, e.g., by its relative position on the TLC plate and, wherein the position on the plate is measured in cm from the base line of the plate or by its relative position in the chromatogram of the HPLC, where the position in a chromatogram is conventionally measured in minutes between injection of the sample on the column and elution of the particular component through the detector. The relative position in the chromatogram is known as the "retention time."

The retention time can vary about a mean value based upon the condition of the instrumentation, as well as many other factors. To mitigate the effects such variations have upon accurate identification of an impurity, practitioners use the "relative retention time" ("RRT") to identify impurities. (Strobel p. 922). The RRT of an impurity is its retention time divided by the retention time of a reference marker. It may be advantageous to select a compound other than the API that is added to, or present in, the mixture in an amount sufficiently large to be detectable and sufficiently low as not to saturate the column, and to use that compound as the reference marker for determination of the RRT.

Those skilled in the art of drug manufacturing research and development understand that a compound in a relatively pure state can be used as a "reference standard." A reference standard is similar to a reference marker, which is used for qualitative analysis only, but is used to quantify the amount of the compound of the reference standard in an unknown mixture, as well. A reference standard is an "external standard," when a solution of a known concentration of the reference standard and an unknown mixture are analyzed using the same technique. (Strobel p. 924, Snyder p. 549, Snyder, L. R.; Kirkland, J. J. Introduction to Modern Liquid Chromatography, 2nd ed. (John Wiley & Sons: New York 1979)). The amount of the compound in the mixture can be determined by comparing the magnitude of the detector response. See also U.S. Pat. No. 6,333,198, incorporated herein by reference.

The reference standard can also be used to quantify the amount of another compound in the mixture if a "response factor," which compensates for differences in the sensitivity of the detector to the two compounds, has been predetermined. (Strobel p. 894). For this purpose, the reference standard is added directly to the mixture, and is known as an "internal standard." (Strobel p. 925, Snyder p. 552).

The reference standard can serve as an internal standard when, without the deliberate addition of the reference standard, an unknown mixture contains a detectable amount of the reference standard compound using the technique known as "standard addition."

In the "standard addition technique", at least two samples are prepared by adding known and differing amounts of the internal standard. (Strobel pp. 391-393, Snyder pp. 571, 572). The proportion of the detector response due to the reference standard present in the mixture without the addition can be determined by plotting the detector response against the amount of the reference standard added to each of the samples, and extrapolating the plot to zero concentration of the reference standard. (See, e.g., Strobel, FIG. 11.4 p. 392). The response of a detector in HPLC (e.g. UV detectors or refractive index detectors) can be and typically is different for each compound eluting from the HPLC column. Response factors, as known, account for this difference in the response signal of the detector to different compounds eluting from the column.

As is known by those skilled in the art, the management of process impurities is greatly enhanced by understanding their chemical structures and synthetic pathways, and by identifying the parameters that influence the amount of impurities in the final product.

The detection or quantification of the reference standard serves to establish the level of purity of the API or intermediates thereof. Use of a compound as a standard requires recourse to a sample of substantially pure compound.

Because the prior art processes do not efficiently remove certain impurities, there is a need for improved methods of purifying montelukast. In particular, the present inventors have isolated the dehydro-montelukast impurity and provided improved purification methods that reduce the level of this and other impurities in montelukast.

SUMMARY OF THE INVENTION

In one embodiment, the present invention provides montelukast sodium containing less than 0.14% MLK-SO by weight. Preferably, the montelukast sodium contains less than about 0.10% MLK-SO by weight.

In another embodiment, the present invention provides montelukast containing less than 0.10% MLK-D by weight. Preferably, the montelukast sodium contains less than about 0.08% MLK-D by weight.

In yet another embodiment, the present invention provides a process for preparing pure montelukast sodium salt comprising: providing a montelukast free acid; converting the montelukast free acid to the di-n-propylamine montelukast salt; and converting the di-n-propylamine montelukast salt to montelukast sodium salt. Preferably, the pure montelukast sodium salt contain less than 0.14% MLK-SO by weight. More preferably, the pure montelukast sodium salt contains less than about 0.10% MLK-SO by weight. Preferably, the pure montelukast sodium salt contains less than 0.10% MLK-D by weight. More preferably, the pure montelukast sodium salt contains less than about 0.08% MLK-D by weight.

In one embodiment, the present invention provides a newly isolated impurity, [R-(E)]-1-[[[1-[3-[2-(7-chloro-2-quinolinyl)ethenyl]phenyl]-3-[2-(1-propenyl)phenyl]propyl]thio]methyl]cyclopropaneacetic acid (MLK-D) of the following structure:

In another embodiment, the present invention provides montelukast sodium containing less than 0.14%, preferably, less than about 0.10%, and more preferably, less than about 0.06% of MLK-SO by weight.

In yet another embodiment, the present invention provides montelukast containing less than about 0.10%, preferably, less than about 0.08% of MLK-D by weight.

In one embodiment, the present invention provides a process of determining the presence of a compound in a sample comprising carrying out HPLC or TLC with MLK-D as a reference marker.

In another embodiment, the present invention provides a process of determining the presence of MLK-D in a sample comprising carrying out HPLC or TLC with the MLK-D as a reference marker. Specifically, this process comprises:

(a) determining by HPLC or TLC the retention time corresponding to MLK-D in a reference marker comprising the MLK-D;

(b) determining by HPLC or TLC the retention time corresponding to MLK-D in a sample comprising montelukast sodium and MLK-D; and (c) determining the presence of MLK-D in the sample by comparing the retention time of step (a) to the retention time of step (b).

In yet another embodiment, the present invention provides present invention provides a process of determining the amount of a compound in a sample comprising carrying out HPLC or TLC with MLK-D as a reference standard.

In one embodiment, the present invention provides a method of quantifying the amount of MLK-D in a sample comprising performing a HPLC or TLC, wherein MLK-D is used as a reference standard. Specifically, this process comprises the steps of:

(a) measuring by HPLC or TLC, the area under a peak corresponding to MLK-D in a reference standard comprising a known amount of MLK-D;

(b) measuring by HPLC or TLC, the area under a peak corresponding to MLK-D in a sample comprising MLK-D and montelukast sodium; and (c) determining the amount of MLK-D, in the sample by comparing the area of step (a) to the area of step (b).

In another embodiment, the present invention provides present invention also provides a process for preparing montelukast from montelukast sodium having less than about 0.10% area by HPLC of MLK-D is present which comprises the steps of:

(a) obtaining one or more samples of one or more batches of montelukast sodium;

(b) measuring the level of MLK-D in each of the samples;

(c) selecting a batch from step a) having a level of MLK-D of about less than 0.10 area % by HPLC, based on the measurement of the samples from the batches; and (d) using the selected batch to prepare montelukast sodium.

In yet another embodiment, the present invention provides a method for isolating MLK-D. The method comprises: providing a solution containing MLK-D, montelukast free acid, and a solvent; precipitating montelukast free acid from the solution; and isolating MLK-D. Suitable solvents include, but are not limited to, at least one of an alcohol, preferably methanol, a halogenated hydrocarbon, a $C_5$-$C_8$ aromatic hydrocarbon, or an ester. Preferably, the method further includes a step of concentrating the solution containing MLK-D. Concentrating the solution can be performed, for example, by evaporating the solvent. Preferably, isolating MLK-D is performed by a chromatographic technique known in the art.

In one embodiment, the present invention provides pharmaceutical formulations comprising the stable MLK-Na of the present invention, and a pharmaceutically acceptable excipient.

In another embodiment, the present invention provides a process for preparing a pharmaceutical formulation comprising combining stable MLK-Na of the present invention with at least one pharmaceutically acceptable excipient.

In yet another embodiment, the present invention provides the use of stable MLK-Na of the present invention for the manufacture of a pharmaceutical composition.

DETAILED DESCRIPTION OF THE INVENTION

Figure 1:
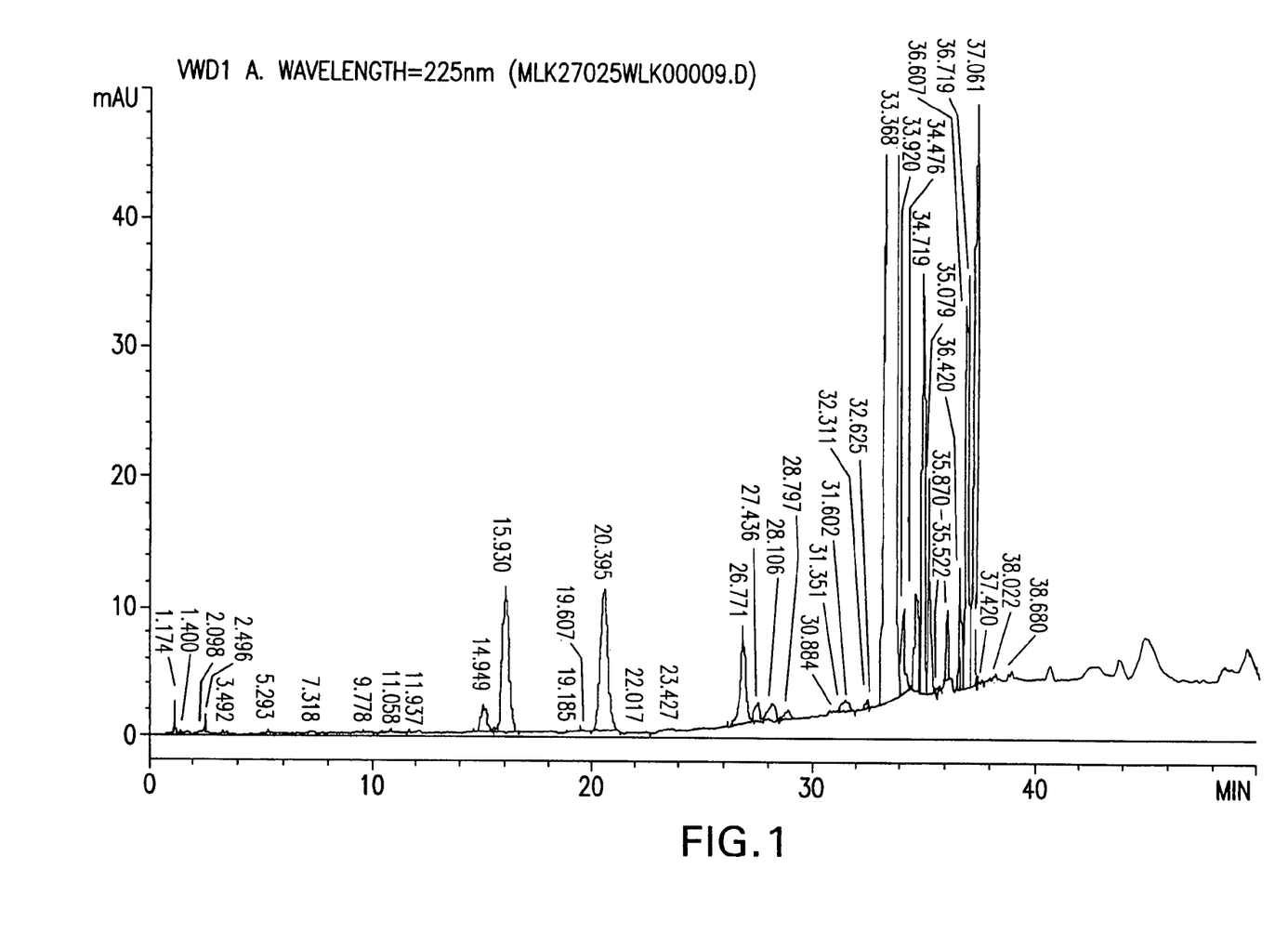
FIG. 1 illustrates an HPLC chromatogram of montelukast sodium.
Figure 2:
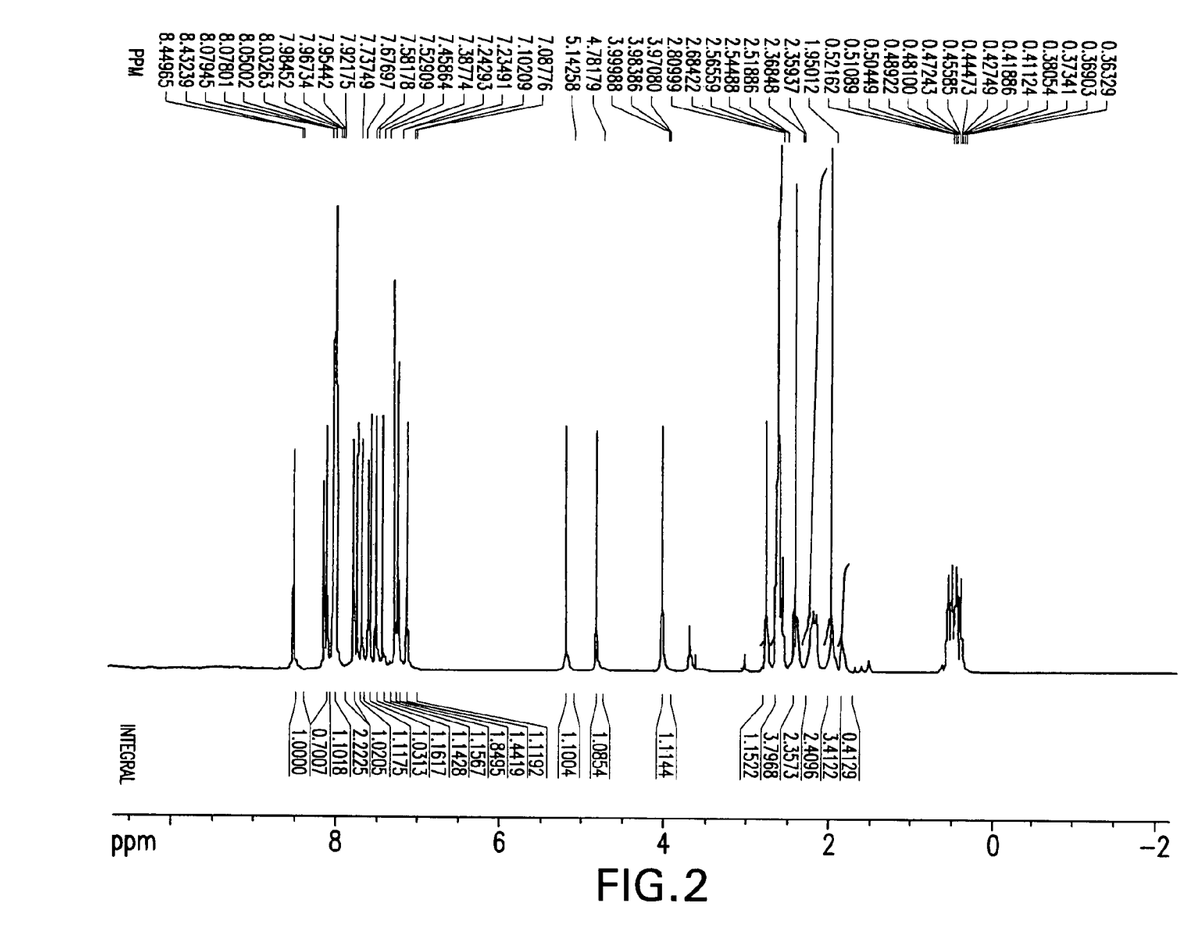
FIGS. 2 and 3 depict NMR spectra for dehydro-montelukast in dimethylsulfoxide.
Figure 3:
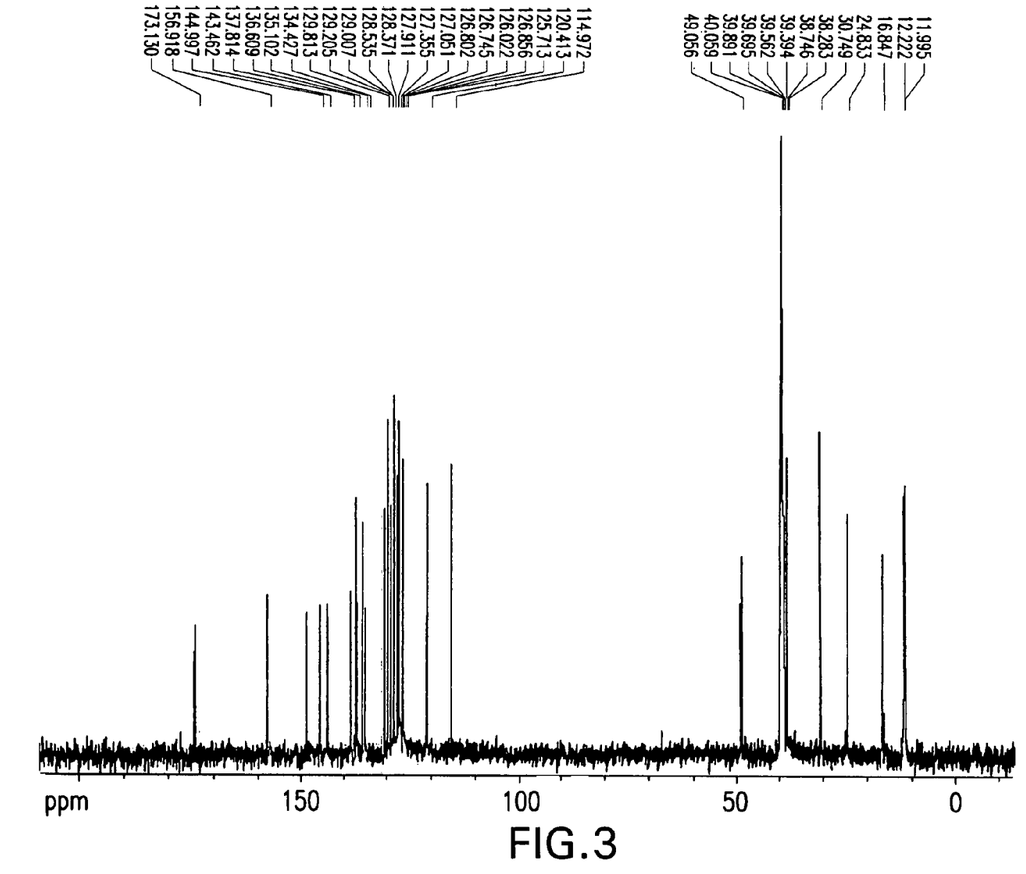
Figure 4:
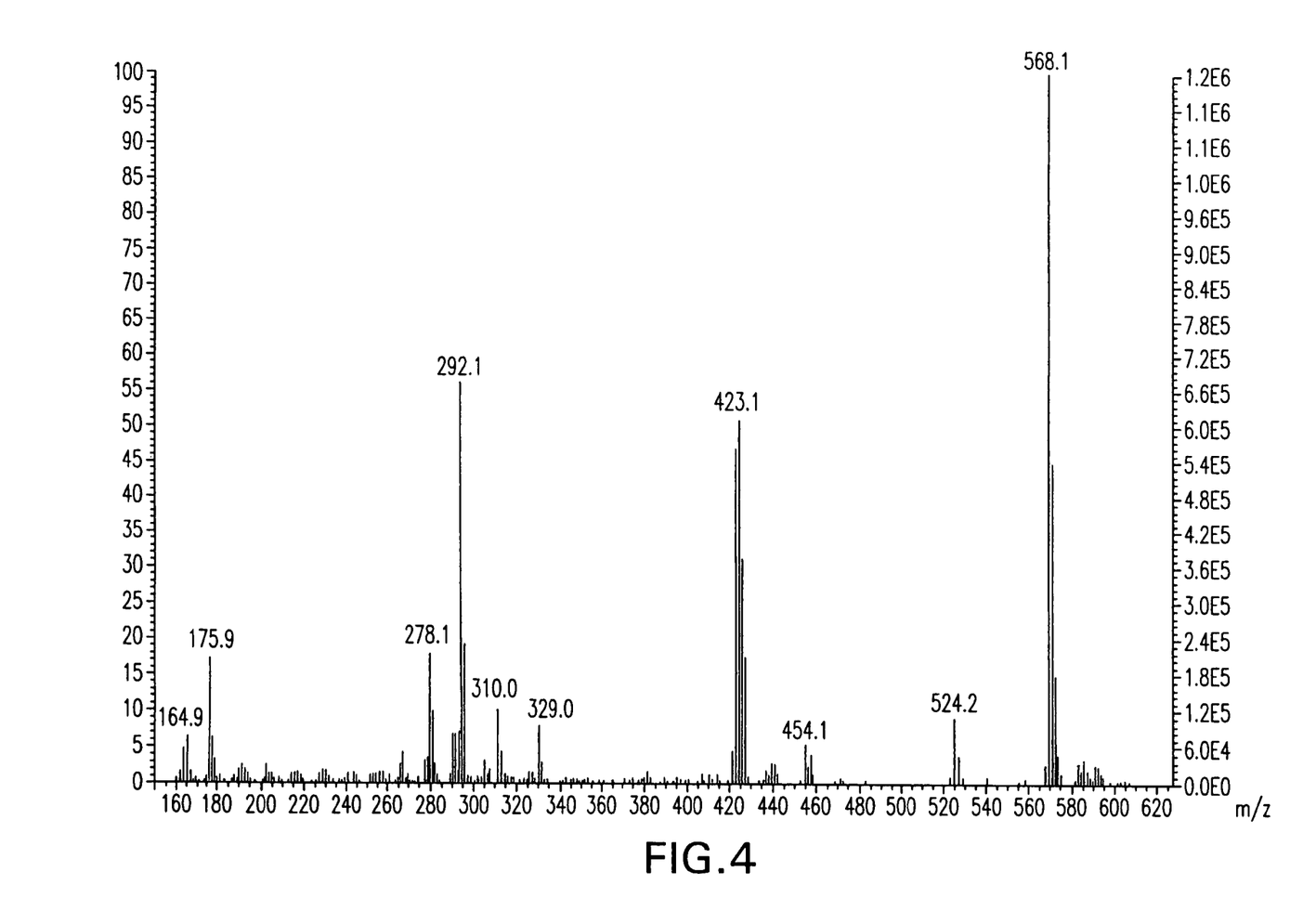
FIG. 4 depicts a fast atom bombardment ionization (FAB) mass spectrum of dehydro-montelukast.
Figure 5:
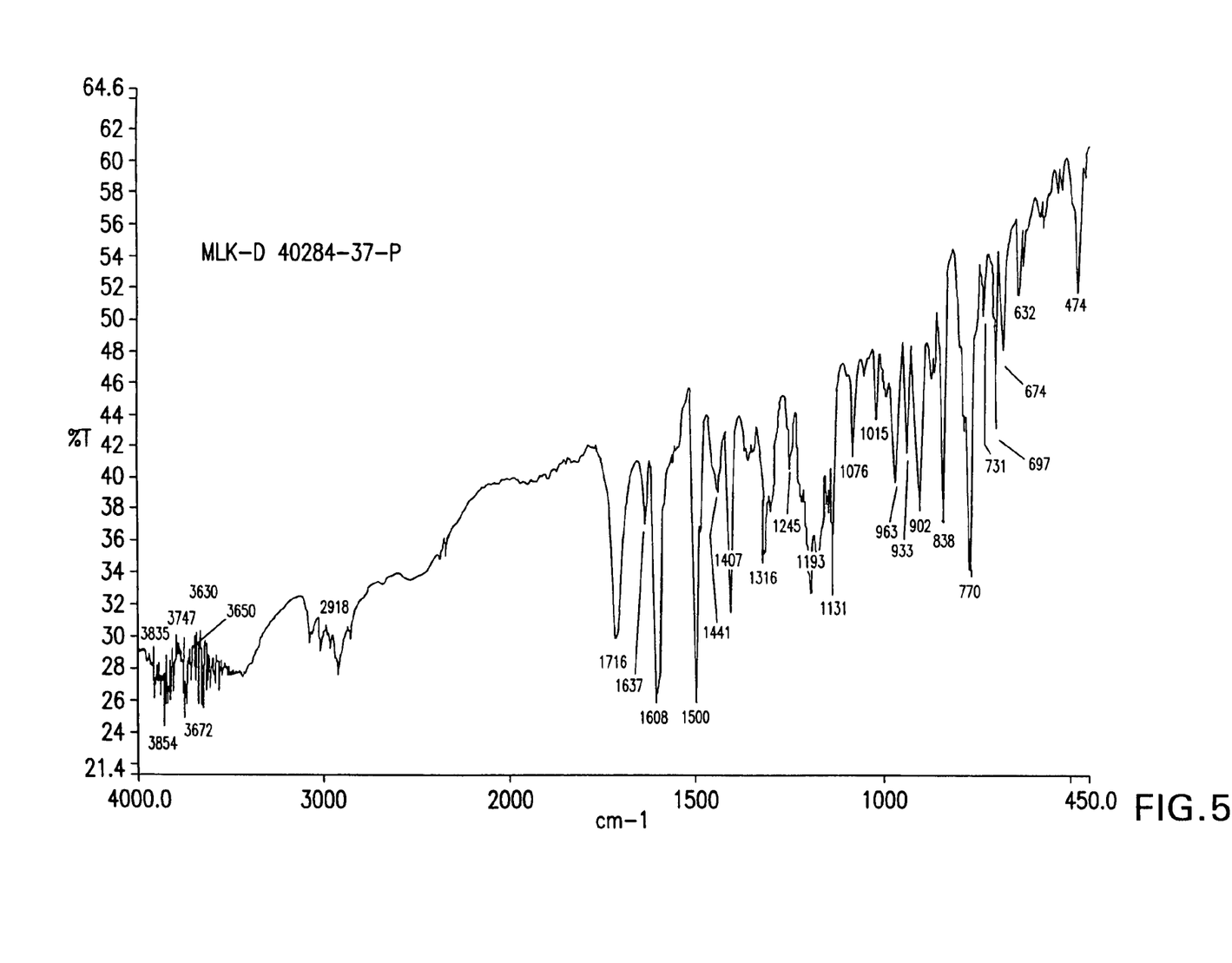
FIG. 5 illustrates an NMR spectrum of dehydro-montelukast.

The process of preparing montelukast sodium salt via the dicyclohexylamine salt as described in U.S. Pat. Nos. 5,614,632 and 6,320,052 is not efficient in removing particular impurities, including montelukast S-monoxide and dehydro-montelukast (D-MLK). In fact, the dehydro-montelukast impurity had not yet been identified.

The present invention relates to methods of purifying montelukast comprising converting montelukast free acid to montelukast di-n-propylamine salt and converting the montelukast di-n-propylamine salt to montelukast sodium salt. The conversion to the di-n-propylamine salt is useful to reduce the level of impurity MLK-D and the impurity, which is described in detail further below.

As used herein the term "MLK-D" refers to [R-(E)]-1-[[[1-3-[2-(7-chloro-2-quinolinyl)ethenyl]phenyl]-3-[2-(1-propenyl)phenyl]propyl]thio]methyl]cyclopropaneacetic acid.

As used herein the term "MLK-SO" refers to [R-(E)-1-[[[3-[2-(7-chloro-2-quinolinyl)ethenyl]phenyl]-3-[2-(1-hydroxy-1-methylethyl)phenyl]propyl]thio]methyl]cyclopropaneacetic acid S-monoxide.

As used herein the term "MLK-Na" refers to [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic sodium salt.

As used herein, the term "relative retention times" (RRT) refers to a ratio of the amount of time a compound elutes from a column relative to MLK-Na.

The present invention provides montelukast sodium containing less than 0.14% MLK-SO by weight. Preferably, the montelukast sodium contains less than about 0.10% MLK-SO by weight.

The present invention provides montelukast containing less than 0.10% MLK-D by weight. Preferably, the montelukast sodium contains less than about 0.08% MLK-D by weight.

The present invention provides a process for preparing pure montelukast sodium salt comprising: providing a montelukast free acid; converting the montelukast free acid to the di-n-propylamine montelukast salt; and converting the di-n-propylamine montelukast salt to montelukast sodium salt. Preferably, the pure montelukast sodium salt contain less than 0.14% MLK-SO by weight. More preferably, the pure montelukast sodium salt contains less than about 0.10% MLK-SO by weight. Preferably, the pure montelukast sodium salt contains less than 0.10% MLK-D by weight. More preferably, the pure montelukast sodium salt contains less than about 0.08% MLK-D by weight.

Optionally, the process may further comprise converting the montelukast free acid to an isopropylamine montelukast salt; and converting the isopropylamine montelukast salt to di-n-propylamine montelukast salt. This optional step of obtaining montelukast isopropylamine salt is useful to remove the S-enantiomer of montelukast. The process for preparing montelukast isopropylamine salt may comprise combining isopropylamine with montelukast free acid. Preferably, the isopropylamine is combined with the solution of montelukast free acid in an organic solvent. Preferably, the organic solvent is 2-butanone. Optionally, the montelukast isopropylamine salt is obtained by crystallizing it from a $C_5$-$C_8$ aromatic solvent or a ketone, more preferably, from 2-butanone. The resulting montelukast isopropylamine salt can be isolated by any means known in the art including, but not limited to, filtering, centrifuging, or decanting.

Preferably, the obtained montelukast isopropylamine salt is dissolved in at least one organic solvent selected from the group consisting of: ether, aromatic solvent, and a saturated hydrocarbon. Preferably, the ether is THF. Preferably, the aromatic solvent is a $C_5$-$C_8$ aromatic solvent. Preferably, the saturated hydrocarbon is a $C_5$-$C_8$ saturated hydrocarbon.

More preferably, the aromatic solvent is toluene. The most preferred solvent is a mixture of toluene and THF.

The montelukast isopropylamine salt may be converted back to the free acid by acidifying the solution. Preferably, the solution is acidified by adding acetic acid.

Preferably, the montelukast free acid or the montelukast isopropylamine salt is converted to montelukast di-n-propylamine salt by dissolving the montelukast free acid or the montelukast isopropylamine salt in at least one of an ether, an aromatic solvent, or a saturated hydrocarbon and adding di-n-propylamine. Preferably, the solvent is toluene or THF. Preferably, the molar ratio of montelukast free acid to montelukast di-n-propylamine is about 1:2. The resulting montelukast di-n-propylamine salt can be isolated by any means known in the art including, but not limited to, filtering, centrifuging, or decanting. Preferably, the montelukast di-n-propylamine salt is crystallized from at least one of a $C_5$-$C_8$ aromatic solvent, preferably toluene; or a saturated $C_5$-$C_8$ hydrocarbon.

The method can also proceed without the isolation of the isopropylamine salt.

Preferably, the process for preparing montelukast sodium salt from di-n-propylamine montelukast salt comprises: dissolving the montelukast di-n-propylamine salt in at least one of a $C_5$-$C_8$ aromatic solvent or a saturated $C_5$-$C_8$ hydrocarbon; acidifying the solution with an acid to form montelukast free acid; and adding at least one source of sodium ion to form montelukast sodium salt. Preferably, the aromatic solvent is toluene. Preferably, the acid is acetic acid.

The montelukast free acid can be prepared by any method known in the art. See, for example, U.S. application Ser. No. 11/048,276, filed Jan. 31, 2005, and Ser. No. 11/112,790, filed on Apr. 21, 2005, both of which are incorporated herein by reference. The montelukast free acid can be an isolated solid form or prepared in situ. Preferably, the montelukast free acid is prepared in situ. For example, montelukast free acid can be prepared by reacting 1-(mercaptomethyl)cyclopropaneacetic acid methyl ester (CYTAM) with 2-(2-(3(S)-(3-(7-chloro-2-quinolinyl)-ethenyl)phenyl)-3-methanesulfonyl oxypropyl) phenyl-2-propanol (mesylate). For the subsequent conversion step, the starting materials for the in situ preparation or the montelukast free acid can be dissolved in an organic solvent. In either case, the organic solvent is at least one of an ether, an aromatic solvent, or a saturated hydrocarbon. Preferably, the ether is tetrahydrofuran (THF); the aromatic solvent a $C_5$-$C_8$ aromatic solvent, and the saturated hydrocarbon is a $C_5$-$C_8$ hydrocarbon. Most preferably, the aromatic solvent is toluene.

The present invention provides a newly isolated impurity, [R-(E)]-1-[[[1-[3-[2-(7-chloro-2-quinolinyl)ethenyl]phenyl]-3-[2-(1-propenyl)phenyl]propyl]thio]methyl]cyclopropaneacetic acid (MLK-D) of the following structure:

having the formula $C_{35}H_{34}C_1NO_2S$ and a molecular weight of 567.90. The impurity MLK-D can be characterized by an RRT at about 1.65 in relation to MLK-Na.

The present invention provides montelukast sodium containing less than 0.14%, preferably, less than about 0.10%, and more preferably, less than about 0.06% of MLK-SO by weight.

The present invention further provides montelukast containing less than about 0.10%, preferably, less than about 0.08% of MLK-D by weight.

Analysis of the tablet shows a level of impurities of about 0.17% of MLK-SO by weight, and about 0.10% of MLK-D by weight The present invention further provides a process of determining the presence of a compound in a sample comprising carrying out HPLC or TLC with MLK-D as a reference marker.

The present invention also provides a process of determining the presence of MLK-D in a sample comprising carrying out HPLC or TLC with the MLK-D as a reference marker. Specifically, this process comprises:

(a) determining by HPLC or TLC the retention time corresponding to MLK-D in a reference marker comprising the MLK-D;

(b) determining by HPLC or TLC the retention time corresponding to MLK-D in a sample comprising montelukast sodium and MLK-D; and (c) determining the presence of MLK-D in the sample by comparing the retention time of step (a) to the retention time of step (b).

The present invention provides a process of determining the amount of a compound in a sample comprising carrying out HPLC or TLC with MLK-D as a reference standard.

The present invention further provides a method of quantifying the amount of MLK-D in a sample comprising performing a HPLC or TLC, wherein MLK-D is used as a reference standard. Specifically, this process comprises the steps of:

(a) measuring by HPLC or TLC, the area under a peak corresponding to MLK-D in a reference standard comprising a known amount of MLK-D;

(b) measuring by HPLC or TLC, the area under a peak corresponding to MLK-D in a sample comprising MLK-D and montelukast sodium; and (c) determining the amount of MLK-D, in the sample by comparing the area of step (a) to the area of step (b).

The present invention also provides a process for preparing montelukast from montelukast sodium having less than about 0.10% area by HPLC of MLK-D is present which comprises the steps of:

(a) obtaining one or more samples of one or more batches of montelukast sodium;

(b) measuring the level of MLK-D in each of the samples;

(c) selecting a batch from step a) having a level of MLK-D of about less than 0.10 area % by HPLC, based on the measurement of the samples from the batches; and (d) using the selected batch to prepare montelukast sodium.

The present invention provides a method for isolating MLK-D. The method comprises: providing a solution containing MLK-D, montelukast free acid, and a solvent; precipitating montelukast free acid from the solution; and isolating MLK-D. Suitable solvents include, but are not limited to, at least one of an alcohol, preferably methanol, a halogenated hydrocarbon, a $C_5$-$C_8$ aromatic hydrocarbon, or an ester. Preferably, the method further includes a step of concentrating the solution containing MLK-D. Concentrating the solution can be performed, for example, by evaporating the solvent. Preferably, isolating MLK-D is performed by a chromatographic technique known in the art.

The present invention also provides pharmaceutical formulations comprising the stable MLK-Na of the present invention, and a pharmaceutically acceptable excipient.

The present invention further provides a process for preparing a pharmaceutical formulation comprising combining stable MLK-Na of the present invention with at least one pharmaceutically acceptable excipient.

The present invention further provides the use of stable MLK-Na of the present invention for the manufacture of a pharmaceutical composition.

Methods of administration of a pharmaceutical composition of the present invention can be administered in various preparations depending on the age, sex, and symptoms of the patient. The pharmaceutical compositions can be administered, for example, as tablets, pills, powders, liquids, suspensions, emulsions, granules, capsules, suppositories, injection preparations (solutions and suspensions), and the like.

Pharmaceutical compositions of the present invention can optionally be mixed with other forms of MLK-Na and/or other active ingredients. In addition, pharmaceutical compositions of the present invention can contain inactive ingredients such as diluents, carriers, fillers, bulking agents, binders, disintegrants, disintegration inhibitors, absorption accelerators, wetting agents, lubricants, glidants, surface active agents, flavoring agents, and the like.

Diluents increase the bulk of a solid pharmaceutical composition, and may make a pharmaceutical dosage form containing the composition easier for the patient and care giver to handle. Diluents for solid compositions include, for example, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, stable MLK-Na and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxy toluene, butylated hydroxyanisole, and ethylenedi amine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

When preparing injectable (parenteral) pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic. Additional ingredients, such as dissolving agents, buffer agents, and analgesic agents may be added.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water that causes the powders to clump into granules. The granulate is screened and/or milled, dried and then screened and/or milled to the desired particle size. The granulate may then be tabletted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

Having described the invention with reference to certain preferred embodiments, other embodiments will become apparent to one skilled in the art from consideration of the specification. The invention is further defined by reference to the following examples describing in detail the preparation of the compound of the present invention. It will be apparent to those skilled in the art that many modifications, both to materials and methods, may be practiced without departing from the scope of the invention.

Instruments

Impurity Profile Determination of Montelukast Sodium by HPLC

| HPLC was performed using the following specifications: | |
| --- | --- |
| Column and packing: | LUNA C18(2) 100A 250 × 4.6 mm, 5 µm, P.N. 00-G-4252-E0 |
| Buffer: | Solution I: 3 ml TFA diluted to 100 ml with water Solution II: 3 ml TFA diluted to 100 ml with acetonitrile |
| Eluent A: | 1 ml of solution I to 2 L water |
| Eluent B: | 1 ml of solution II to 2 L acetonitrile |

| Gradient of Eluent: | | |
| --- | --- | --- |
| Time (min) | Eluent A (%) | Eluent B (%) |
| 0 | 38 | 62 |
| 10 | 35 | 65 |
| 20 | 35 | 65 |
| 35 | 5 | 95 |
| 40 | 5 | 95 |

| | |
| --- | --- |
| Stop time: | 40 min |
| Equilibration time: | 10 min |
| Flow: | 1.5 ml/min |
| Detector: | 225 min |
| Injection volume: | 20 µl |
| Diluent: | 80% acetonitrile: 20% water |
| Column temperature: | 25° C. |
| Autosampler temperature: | 5° C. |

EXAMPLES

Example 1

The preparation of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid A cold solution of the mesylate (2-(2-(3(S)-(3-(7-chloro-2-quinolinyl)-ethenyl)phenyl)-3-methanesulfonyl oxypropyl)phenyl-2-propanol) (about −5° C., 38 ml) was prepared from 10.1 g of the diol (MKT) ((S)-1-[[[1-[3-[2(E)-(7-chloro-2-quinolinyl) ethenyl]phenyl]]-3-[2-(1-hydroxy-1-methylethyl)phenyl]-1-propanol)). The mesylate solution was added to a cold solution of CYTAM (1-(mercaptomethyl)cyclopropaneacetic acid methyl ester) (5.05 g) in N,N-dimethylacetamide (−7° C., 20 ml). 47% NaOH (4.55 g) was added dropwise for 9 min, under intensive stirring. The reaction was exothermic; the temperature rose to −1° C. The clear, viscous reaction mixture was stirred for 1 h at −6° C., 1.5 h at 18° C., and heated to 38° C. in one hour. 47% NaOH (5.12 g) was added all at once and stirred overnight at 38° C. The reaction mixture (liquid with solid) was quenched with 5% NaCl (50 ml) under stirring at 38° C. The aqueous lower phase was separated and discarded. The organic phase was diluted with THF (30 ml) and washed with 5% NaCl (50 ml). The aqueous phase was separated and discarded. The organic phase was diluted with THF (10 ml) and treated with 7.5% tartaric acid (50 ml) to adjust the pH to 3-5. The aqueous phase was separated and discarded. The organic solution was directly used in the next step.

Example 2

Enantiomeric purification by the preparation of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid isopropylamine salt Isopropylamine (1.95 g) was added to the reaction mixture from the previous example. The clear reaction solution was stirred for 0.5 h at room temperature, and volatiles were removed by evaporation in a 55° C. bath under reduced pressure (20 mbar). The oily residue was dissolved in methylethylketone (40 ml) at 50° C., and the residual THF was stripped off with methylethylketone. The operation was repeated.

The residue, a heavy oil, was dissolved in hot methylethylketone (120 ml) at 71° C. The clear solution was gradually cooled for 0.5 h to 37° C. to induce crystallization. The suspension was held for 0.5 h at this temperature and gradually cooled to 0° C. in 1 h. The mixture was held for 1.3 h at 0° C. and filtered. The cake was washed with cold methylethylketone (0° C., 50 ml) to afford 21.22 g wet product, which was dried overnight at room temperature and for 3 h at 50° C. under reduced pressure (20 mbar) to afford 9.5 g of the dried crude product as an off-white solid (purity 98.4%).

The isolated yield was 68% relative to MKT. The level of S-enantiomer was reduced from 0.28% to an undetectable level. The level of MLK-SO was reduced from 0.16% to 0.09%.

Example 3

3-[2-(1-hydroxy-1-methylethyl)phenyl]propyl]thio]methyl]cyclopropyl acetic acid Isopropyammonium salt (MLK-IPAM)

S-MKT (4 kg) is reacted with methanesulfonyl chloride (1.4 kg) in the presence of DIPEA (2.2 Kg) in THF as solvent (20 liter) to yield the mesylate compound. During the reaction, the diisopropylethylamine hydrochloride (DIPEA•HCl) salt is formed. The salt is removed by filtration. The mother liquor, the THF solution of MKT-Mesylate, is then reacted with CYTAM (2.4 kg) in the presence of sodium hydroxide (2 kg) in a mixture of THF and DMA (4 L) to yield a solution of R-MLK-Me.

After the isolation step, the reaction mixture is heated gradually to 40° C. and treated with an additional amount of sodium hydroxide (2 kg). The solution is mixed for about 4 hrs to induce the hydrolysis of R-MLK-Me and yield the R-MLK-Na. The DMA and the other side products are removed by twice washing the reaction mixture with a dilute NaCl solution (each washing is with 20 liters of 5% NaCl solution) to afford the THF solution of crude MLK-Na.

The reaction mixture is acidified with a dilute aqueous solution of tartaric acid (7.5%) until a pH of 3-4 is reached to yield MLK-H. The aqueous phase is separated to afford a THF solution of the crude MLK-H. The aqueous solution containing tartaric acid salts is discarded.

The THF solvent is removed by distillation at 50° C. under vacuum until dry. The residue (a sticky foam) is dissolved in methyl-ethyl-ketone (MEK) and cooled to <30° C. 0.78 kg of i-Propylamine (IPAM) is added and after cooling a salt, MLK-IPAM, precipitates from solution. The solid is filtered off, washed with MEK, and used in the next stage. Optionally depending on the purity the solid is recrystallized from MEK and optionally dried.

Example 4

The purification of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid via the crystallization of di-n-propylamine salt The crude [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid isopropylamine salt (8.51 g) was dissolved in a mixture of toluene (40 ml) and THF (10 ml) and treated by glacial acetic acid (1.42 g) to adjust the pH to 5-6. The reaction mixture was stirred for 40 minutes and washed with water (20 ml). The aqueous phase was separated and discarded. Di-n-propylamine (2.74 g) was added to the organic phase, and the clear reaction solution was stirred for 0.5 h at room temperature. Volatiles were removed by evaporation at 55° C. under reduced pressure (20 mbar). The residue, a heavy oil, was dissolved in toluene (40 ml), and residual THF was stripped off with toluene.

The residue was dissolved in toluene (35 ml) at 40° C. The clear solution was gradually cooled to 25° C. to induce crystallization. The mixture was held for 0.5 h at this temperature and slowly cooled to 0° C. The suspension was stirred overnight and was filtered. The cake was washed with cold (0°) toluene to afford 7.3 g of the wet product. The wet product was dried for 3.5 h at 50° C. under reduced pressure (20 mbar) to afford 7.2 g of the dried crystalline product as an off-white solid (purity 99.7%).

The isolated yield was 53% relative to MKT.

Example 5

The purification of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid via the crystallization of di-n-propylamine salt The montelukast acid of Example 1 can also be directly transformed to the di-n-propylamine salt. The organic solution obtained by Example 1 is evaporated to dryness, and the residue is dissolved in toluene as in Example 4. The remaining steps of Example 3 are performed to yield the di-n-propylamine salt.

The amount of MLK-D was reduced from 0.95% to a level of 0.03-0.08% by weight. The amount of MLK-SO was reduced to a level of 0.04-0.06% by weight.

Example 6

Preparation of crystalline 1-[[[[1(R)-[3[2-(7-chloro 2-quinolinyl)-ethenyl]phenyl]]3-[2-(1-hydroxy-1-methylethyl)phenyl]propyl]thio]methyl]cyclopropyl acetic acid di-n-propylamine salt (MLK-DPA)

500 g of MLK-IPAM is dissolved in 2 L of THF at room temperature and 1 L of a tartaric acid solution in water 7.5% is added reaching a pH of 3-5. The phases are separated and the water phase is discarded. THF is removed by distillation under vacuum at <60° C. until dry. The residue (sticky foam) is dissolved by the addition of toluene and cooled. 118 g of di-n-propylamine (DPA) is added inducing after further cooling with eventual seeding the precipitation of the crude salt, MLK-DPA. The solid is filtered washed twice with toluene and without drying recrystallized from toluene. The crystallized MLK-DPA is dried in a vacuum oven at 45-55° C.

Example 7

The preparation of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic sodium salt A 500 ml flask equipped with mechanic stirrer was charged with toluene (225 ml) and montelukast di-n-propylamine salt (45 g). The suspension was stirred at ambient temperature for 30 minutes. Sodium tert-butoxide (6.5 g) was added to the suspension, and the reaction mixture was stirred at 30-40° C. for 30 minutes. Active carbon (2 g) was added, and the solution was filtered over active carbon.

The mixture was added portionwise to a flask containing heptane (630 ml) to form a precipitate, and the mixture was further stirred at ambient temperature for 1 hour.

The montelukast sodium salt crystals were collected by filtration, washed with heptane, and dried at 45° C. under reduced pressure. Montelukast sodium (32 g) was obtained as an amorphous material containing greater than 1% water. The amount of MLK-D was reduced to an undetectable level.

Example 8

Isolation of MLK-D

MLK-D was isolated by flash chromatography from the residue of Examples 3-5. The mobile phase is CHCl$_3$:ether (8:2). Mother liquor (ML) from the reactions of Examples 3-5 was concentrated by evaporating the solvent under reduced pressure at 45° C. The oily residue was dissolved with a small amount of MeOH and stirred overnight at room temperature. The MLK-H precipitate was filtrated, and the ML was again concentrated by evaporating the solvent under reduced pressure at 45° C. The residue was dissolved in minimum amount of CHCl$_3$:ether (8:2), then charged on the silica gel. Multiple fractions were collected to obtain the MLK-D sample.

Example 9

The Use of MLK-D as a Reference Standard and a Reference Marker

A mixture containing 0.025 mg/ml montelukast sodium (MLK-Na) standard and 0.025 mg/ml MLK-D marker in diluent was prepared using only amber flasks and vials. The retention time of montelukast sodium was about 20 minutes; the retention time of MLK-D was about 33 minutes.

A standard solution was prepared by dissolving and diluting 10 mg of montelukast sodium standard in a 10 ml volumetric amber flask. This solution was diluted 1/100 and then 1/10 with diluent. A sample solution was prepared by dissolving and diluting 10 mg of montelukast sodium sample in a 10 ml volumetric amber flask.

The standard solution was injected with a stop time of 25 minutes, and the sample solution continuing the chromatogram to the end of the gradient. The area of each impurity was calculated by the formula:

$$\% \text{ Impurity} = \frac{\text{Area impurity} \times \text{Concentration } (MLK-\text{Na}) \text{ std} \times \text{Potency } (MLK-\text{Na}) \text{ std}}{\text{Concentration impurity} \times \text{Area } (MLK-\text{Na}) \text{ std}}$$

| The relative retention times are: | |
|---|---|
| Substance | RRT |
| MLK-SO | 0.35 |
| MLK-Na | 1 |
| MLK-D | 1.65 |

The detection limit for the HPLC method is 0.01%, and the quantification limit is 0.03%.

| Example 10: Repetition of U.S. Pat. No. 5,614,632 | | | | | | | |
|---|---|---|---|---|---|---|---|
| solvent | volume | Amine | yield | MLK-SO | MLK | MLK salt | MLK-D |
| EtOAc | 8 | Cyclohexyl amine 2.05 eq | 92% | 0.32 1.26 | 0.48 0.32 | 1.00 92.22 | 1.45 3.25 |

What is claimed is:

1. Montelukast sodium containing less than 0.14% MLK-SO by weight.

2. Montelukast sodium containing less than 0.10% MLK-D by weight.

3. Montelukast sodium containing less than 0.10% of MLK-SO by weight.

4. Montelukast sodium containing less than about 0.08% of MLK-D by weight.

5. Pharmaceutical formulations comprising the MLK-Na according to claim 1 and a pharmaceutically acceptable excipient.

* * * * *